US007169318B1

(12) United States Patent
Hall

(10) Patent No.: US 7,169,318 B1
(45) Date of Patent: Jan. 30, 2007

(54) IMBIBED ORGANIC LIQUIDS, ESPECIALLY HALOGENATED ORGANICS

(76) Inventor: Richard H. Hall, 1187 E. Stewart Rd., Midland, MI (US) 48642

( * ) Notice: Subject to any disclaimer, the term of this patent is extended or adjusted under 35 U.S.C. 154(b) by 294 days.

(21) Appl. No.: 10/801,773

(22) Filed: Mar. 16, 2004

Related U.S. Application Data

(60) Provisional application No. 60/455,778, filed on Mar. 18, 2003.

(51) Int. Cl.
*A62D 1/02* (2006.01)
*A01M 99/00* (2006.01)
*A62C 39/00* (2006.01)
*A61K 9/14* (2006.01)
*A61K 47/30* (2006.01)

(52) U.S. Cl. ...................... 252/3; 252/8; 43/1; 89/1.11; 169/46; 169/47; 239/6; 239/53; 239/54; 239/55; 239/56; 424/484; 424/485; 424/486; 424/487; 424/488; 424/489; 424/501

(58) Field of Classification Search ..................... None
See application file for complete search history.

(56) References Cited

U.S. PATENT DOCUMENTS 3,147,216 A * 9/1964 Oemler ....................... 210/693
3,750,688 A 8/1973 Hall et al.
4,237,237 A * 12/1980 Jarre et al. .................. 521/128
4,276,179 A * 6/1981 Soehngen .................. 210/679
4,302,337 A 11/1981 Larson et al.
4,573,578 A * 3/1986 Greminger et al. ...... 206/524.4
5,567,416 A * 10/1996 Sato et al. ................. 424/76.4
2001/0020602 A1* 9/2001 Buijtenhuijs et al. ....... 210/690

FOREIGN PATENT DOCUMENTS

EP 23111 A1 * 1/1981
EP 388140 A1 * 9/1990

OTHER PUBLICATIONS

Hall, U.S. Appl. No. 60/455,778 filed on Mar. 18, 2003 A.D.

* cited by examiner

*Primary Examiner*—Matthew A. Thexton
(74) *Attorney, Agent, or Firm*—Christopher John Rudy

(57) ABSTRACT

Solid composition has an organic spill absorbing material in which is absorbed certain of a liquid organic compound or composition. The organic spill absorbing material can be water insoluble, particulate polymer particles that imbibe liquid organic materials. A halogenated organic can provide the liquid organic compound or composition. The halogenated organic can be a halogenated hydrocarbon. A fire can be fought by transmitting the solid composition containing a suitable flame retardant to the base of the fire under conditions such that the absorbed liquid in liquid or vapor form is released; and a living target can be stupefied by transmitting the solid composition containing a suitable stupefying agent under conditions such that vapors of the stupefying agent are released and stupefy the target.

20 Claims, No Drawings

IMBIBED ORGANIC LIQUIDS, ESPECIALLY HALOGENATED ORGANICS

CROSS-REFERENCE PRIORITY CLAIM

This claims benefit under 35 USC 119(e) of U.S. provisional patent application No. 60/455,778 filed on Mar. 18, 2003 A.D. The complete specification of that application is incorporated herein by reference.

FIELD AND PURVIEW

This concerns compositions of organic liquids with an organic spill absorbing material and uses thereof, to include transmittal of the absorbed liquid to the base of a fire to extinguish or control it, or to release a stupefying gas, etc. Of special concern are particulate polymer particles which imbibe liquid organic materials, and halogenated organic liquids.

BACKGROUND

In control of conflagrations such as at an oil well or from spilled fuel, it would be desirable to direct fire extinguishing compound such as a liquid halogenated hydrocarbon, for example, HALON-1211 or FREON-114-B2, to a base of the fire to control it. However, the stream of liquid often never reaches the base of the fire as the outskirts of the flame may vaporize the liquid, and it is drawn up and away from the source of the firestorm.

It would be desirable to ameliorate or overcome such events.

SUMMARY

The present invention provides, in one aspect, a solid composition comprising an organic spill absorbing material in which is absorbed certain of a liquid organic compound or composition. In another aspect, provided are methods of fighting a fire comprising transmitting said solid composition containing a suitable flame retardant to the base of a fire under conditions such that said absorbed liquid in liquid or vapor form is released; and of providing for stupefaction of a living target comprising transmitting said solid composition containing a suitable stupefying agent (stupefyer) under conditions such that vapors of said stupefyer are released and stupefy the target.

The invention is useful in fire and living target control.

Significantly, by the invention, liquid fire retardants such as liquid halogenated hydrocarbons, for instance, certain HALONS and FREONS, can be directed to the base of a conflagration in a solid form, where they can help control the fire in their liquid or vapor state. As well, liquid stupefying agents which act in the vapor state, for instance, 1,1,2-trichloroethylene or chloroform, may be delivered in solid form.

Numerous further advantages attend the invention.

ILLUSTRATIVE DETAIL

The invention may be further understood by the present details. The same as well as the foregoing summary are to be taken in an illustrative and not necessarily limiting sense.

The organic spill absorbing material, in general, is an absorbent. Beneficially, the absorbent is or contains water insoluble, particulate polymer particles which imbibe liquid organic materials. As described in Hall et al., U.S. Pat. No.

3,750,688, on contact with the organic material the absorbent may swell as it is absorbed or imbibed. It may not be critical to employ a cross-linked polymer that swells but does not dissolve. However, cross-linked organic liquid-imbibing polymers are preferred. A wide variety of polymeric materials are employed with benefit. Such polymers include polymers of styrenes and substituted styrenes; copolymers of vinyl chloride including a copolymer of sixty weight percent vinyl chloride and forty weight percent vinyl acetate; vinylidene chloride copolymers including a copolymer of seventy-five percent vinylidene chloride and twenty-five percent acrylonitrile; acrylic polymers such as polymers of methylmethacrylate, ethyl acrylate, and so forth and the like. Particularly advantageous materials which respond to a wide variety of organic liquids are the polymers of styrene such as polystyrene and polymers of styrene and divinylbenzene containing up to ten weight percent divinylbenzene. For general use with aliphatic and aromatic hydrocarbons, alkylstyrene polymers are of particular benefit. When considered for drain or other device shut off systems which employ the imbibing polymers, such alkylstyrene polymers swell very rapidly on contact with aliphatic and/or aromatic hydrocarbons. Generally, the more rapid swelling of the polymer is, the more rapid is the shut off when the organic liquid contaminant is contacted. Alkylstyrene polymers usually show substantial swelling in less than a minute when in contact with organic liquids. Cross-linked polymers of styrenes, notably tertiary-alkylstyrenes, are used to advantage as the imbibing agent. Those alkylstyrenes which can be used to prepare these imbibing polymers have alkyl groups having four to twenty, especially four to twelve, carbon atoms, examples of which include p-tert-, m-tert-, sec-, and/or iso-alkyl styrenes such as of butylstyrene, amlystyrene, hexylstyrene, octylstyrene, dodecylstyrene, octadecylstyrene and eiscosylstyrene. Further, cross-linked copolymers of such alkylstyrenes as aforementioned and an alkyl ester derived from a one to eighteen carbon alcohol and acrylic or methacrylic acid or mixture thereof. Suitable monomers which can be employed as comonomers with the alkylstyrene include such materials as vinylnaphthalene, styrene, alpha-methylstyrene, ring-substituted alpha-methylstyrenes, halostyrenes, arylstyrenes and alkarylstyrenes, methacrylic esters, acrylic esters; esters and half esters of fumaric, maleic, itaconic acids; vinyl biphenyls, vinyl esters of aliphatic carboxylic acid esters, alkyl vinyl ethers, alkyl vinyl ketones, alpha-olefins, iso-olefins, butadiene, isoprene, dimethylbutadiene, acrylobisnitrile, methacrylonitrile, and so forth and the like. A slight amount of cross-linking agent can be contained in the polymer, say, in the range about from 0.01 to two percent by weight. A highly efficient imbibition of organic liquid contaminants occurs when the level of cross-linking agent is less than about one percent by weight since this permits the polymers to swell easily and imbibe a substantial volume of the organic material. When organic liquid-contaminated water is percolated through a packed column or bed of only polymer particles, up to two percent cross-linking agent is satisfactory. Suitable cross-linking agents include polyethylenically unsaturated compounds such as divinylbenzene, diethylene glycol dimethacrylate, diisopropenylbenzene, diisopropenyldiphenyl, diallylmaleate, diallylphthalate, allylacrylates, allymethacrylates, allylfumarates, allylitaconates, alkyd resin type cross-linking agents, butadiene or isoprene polymers, cyclooctadiene, methylene norbornlylenes, divinyl phthalates, vinyl isopropenylbenzene, divinyl biphenyl, as well as any other di- or poly-functional compounds known to be of use as a cross-linking agent in polymerical vinyl addition compositions. If there is too much cross-linking agent, the imbibition takes an unreasonably long time, or the polymer is unable to imbibe a sufficient quantity of the organic liquid, and interstitial spaces in the bed are closed. If the imbibitional polymer contains no or too little cross-linking agent, then it may well eventually dissolve or partially dissolve in the organic material resulting, for example, in a non-discrete, non-particulate mass of polymer-thickened organic liquid. However, for many applications where closure of a line is quickly noticeable, uncrosslinked material is satisfactory. The imbibing polymers may be prepared by any suitable technique. For instance, suspension, emulsion or mass polymerization may be employed. Generally, as is well known in the art, the method of preparation is selected to provide imbibing polymer in the most convenient form for any particular application. A latex polymer such as described in Larson et al., U.S. Pat. No. 4,302,337, or other polymer may be employed as the organic liquid imbibant as well.

Into the organic spill absorbing material is absorbed the liquid organic compound or composition. Any suitable amount of the liquid organic compound or composition in relation to the organic spill absorbing material, may be employed in the practice of the present invention. Preferably, the liquid organic compound or composition is absorbed in an amount that is a significant part or percent of the capacity of the organic spill absorbing material, say, about two to fifty, or about three to forty, or about five to thirty, percent by volume of the carrying capacity of the organic spill absorbing material, if not higher.

Any suitable liquid organic compound or composition may be employed. Employment of a particular liquid organic compound or composition may depend on the purposes for which it is intended, and the properties of the liquid organic compound or composition. Preferably, the liquid organic compound or composition is a halogenated organic. Halogens herein include independently at each occurrence I, Br, Cl and F, especially Br, Cl and/or F. If especially to be employed for fire control, the halogenated organic preferably has at least one Br-moiety per molecule, for example, one as in HALON-1211 which is well known to be carried in liquid form in canisters for aircraft engine fire control, or two or more Br-moieties per molecule as, for example, in FREON 114-B2, although Br-moieties may not be required nor desired since they may diminish the ozone layer. Thus, a chlorinated compound such as tetrachloromethane or even a fluorinated compound including certain other FREON substances may be employed as a fire extinguishing liquid organic compound. For stupefying, which may include inducing a drowsy state in a human or animal, or killing or controlling if needed, especially an animal pest to include an insect, exemplary halogenated organics include 1,1,2-trichloroethylene and chloroform. Advantageously thus, the halogenated organic is a halogenated hydrocarbon.

The solid composition with absorbed, preferably, imbibed, liquid organic compound or composition may be transmitted where needed by any suitable method. As an example, the solid composition with absorbed fire extinguisher may be poured on a fire base manually, by aircraft, towed or pushed on a sled, and so forth; it may be packaged in suitable plastic tubes analogous to those employed to package ground meat for sale and poured on the fire as before, thrown into the fire, or shot by compressed air or slingshot; it may be formulated with an explosive charge so that a package of the solid composition with fire extinguisher would explode when brought into contact with the fire, thus spreading the fire extinguisher at the base of the fire; and so forth. The solid composition with stupefying agent may be simply placed in a room, or on a roof over a room or building, where a living target resides, or poured by aircraft, shot, thrown and so forth as with a solid composition with the fire extinguisher.

CONCLUSION

The present invention is thus provided. Various features, parts, subcombinations and combinations may be employed with or without reference to other features, parts, subcombinations or combinations in the practice of the present invention, and numerous adaptations and modifications may be effected within its spirit, the literal claim scope of which is particularly pointed out as follows:

I claim:

1. A solid composition comprising:

a solid organic spill absorbing material; and a liquid organic compound or composition that is absorbed in said material and includes a halogenated organic including halogen moiety(ies) independently at each occurrence of F, Br, I or a combination thereof;

wherein the solid composition is useful for fighting a fire or for stupefying a living target.

2. The solid composition of claim 1, wherein the organic spill absorbing material includes water insoluble, particulate polymer particles that imbibe liquid organic materials.

3. The solid composition of claim 2, wherein the halogen moiety(ies) consist essentially of independently at each occurrence of F, Br or a combination thereof.

4. The solid composition of claim 1, wherein the halogenated organic is a halogenated hydrocarbon that has at least one Br-moiety per molecule.

5. The solid composition of claim 2, wherein the halogenated organic is a halogenated hydrocarbon that has at least one Br-moiety per molecule.

6. The solid composition of claim 3, wherein the halogenated organic is a halogenated hydrocarbon that has at least one Br-moiety per molecule.

7. The solid composition of claim 1, which is useful for fighting a fire.

8. The solid composition of claim 2, which is useful for fighting a fire.

9. The solid composition of claim 3, which is useful for fighting a fire.

10. The solid composition of claim 4, which is useful for fighting a fire.

11. The solid composition of claim 5, which is useful for fighting a fire.

12. The solid composition of claim 6, which is useful for fighting a fire.

13. The solid composition of claim 2, which is useful for stupefying a living target.

14. A method of fighting a fire comprising transmitting a solid composition, which embraces particles of an organic spill absorbing material in which is absorbed a liquid organic compound or composition that includes a fire fighting agent, to a base of the fire under conditions such that said absorbed liquid in liquid or vapor form is released.

15. The method of claim 14, wherein the organic spill absorbing material includes water insoluble, particulate polymer particles that imbibe liquid organic materials.

16. The method of claim 15, wherein the liquid organic compound or composition is a halogenated organic.

17. The method of claim 16, wherein the halogenated organic has halogen moiety(ies) that consist essentially of independently at each occurrence F, Br or a combination thereof.

18. The method of claim 16, wherein the halogenated organic has at least one Br-moiety per molecule.

19. A method of providing for stupefaction of a living target comprising transmitting a solid composition of water insoluble, particulate polymer particles that imbibe liquid organic materials, in which composition is absorbed as a liquid a stupefying agent, under conditions such that vapors of the stupefying agent are released and stupefy the target.

20. The method of claim 19, wherein the stupefying agent is a halogenated organic.

* * * * *